US010668272B2

(12) United States Patent
Blume et al.

(10) Patent No.: US 10,668,272 B2
(45) Date of Patent: Jun. 2, 2020

(54) COCHLEAR IMPLANT

(71) Applicants: Medizinische Hochschule Hannover, Hannover (DE); Gottfried Wilhelm Leibniz Universitaet Hannover, Hannover (DE)

(72) Inventors: Holger Blume, Wedemark (DE); Wolfgang Ertmer, Garbsen (DE); Thomas Lenarz, Hannover (DE); Andrej Kral, Hannover (DE)

(73) Assignees: MEDIZINISCHE HOCHSCHULE HANNOVER, Hannover (DE), part interest; GOTTFRIED WILHELM LEIBNIZ UNIVERSITAET HANNOVER, Hannover (DE), part interest ( * ) Notice: Subject to any disclaimer, the term of this patent is extended or adjusted under 35 U.S.C. 154(b) by 180 days.

(21) Appl. No.: 15/744,186

(22) PCT Filed: Jul. 27, 2016

(86) PCT No.: PCT/DE2016/100342
§ 371 (c)(1),
(2) Date: Feb. 27, 2018

(87) PCT Pub. No.: WO2017/036441
PCT Pub. Date: Mar. 9, 2017

(65) Prior Publication Data
US 2018/0200504 A1     Jul. 19, 2018

(30) Foreign Application Priority Data

Aug. 31, 2015   (DE) .................. 10 2015 114 514

(51) Int. Cl.
*A61N 1/00*     (2006.01)
*A61N 1/05*     (2006.01)
(Continued)

(52) U.S. Cl.
CPC ....... *A61N 1/0541* (2013.01); *A61N 1/36036* (2017.08); *A61N 1/36038* (2017.08);
(Continued)

(58) Field of Classification Search
CPC ............. A61N 1/0541; A61N 1/36036; A61N 1/36038; A61N 1/36175; A61N 1/36171; H02J 50/10; H02J 50/05
See application file for complete search history.

(56) References Cited

U.S. PATENT DOCUMENTS

| 5,061,282 A | 10/1991 | Jacobs |
|---|---|---|
| 6,575,894 B2 | 6/2003 | Leysieffer et al. |

(Continued)

FOREIGN PATENT DOCUMENTS

DE     100 18 361 A1    10/2001

OTHER PUBLICATIONS

English translation of the International Preliminary Report on Patentability and Written Opinion of the International Searching Authority of PCT/DE2016/100342, dated Mar. 15, 2018.
(Continued)

*Primary Examiner* — Scott M. Getzow
(74) *Attorney, Agent, or Firm* — Collard & Roe, P.C.

(57) ABSTRACT

A cochlear implant of a cochlear implant system is described. The cochlear implant comprises electrodes which are mechanically connected to one another and can be inserted in a row in the form of a spiral into a cochlea in order for auditory nerve receptors to be stimulated, a control circuit that can specifically apply electric pulses to the individual electrodes, and an energy source. The control circuit allows the electrodes to be fed in a pulsed manner with electric signals generated by a processor from the acoustic signals, and auditory nerve receptors adjacent to the electrodes to be stimulated. The electrodes are components
(Continued)

Figure 1:
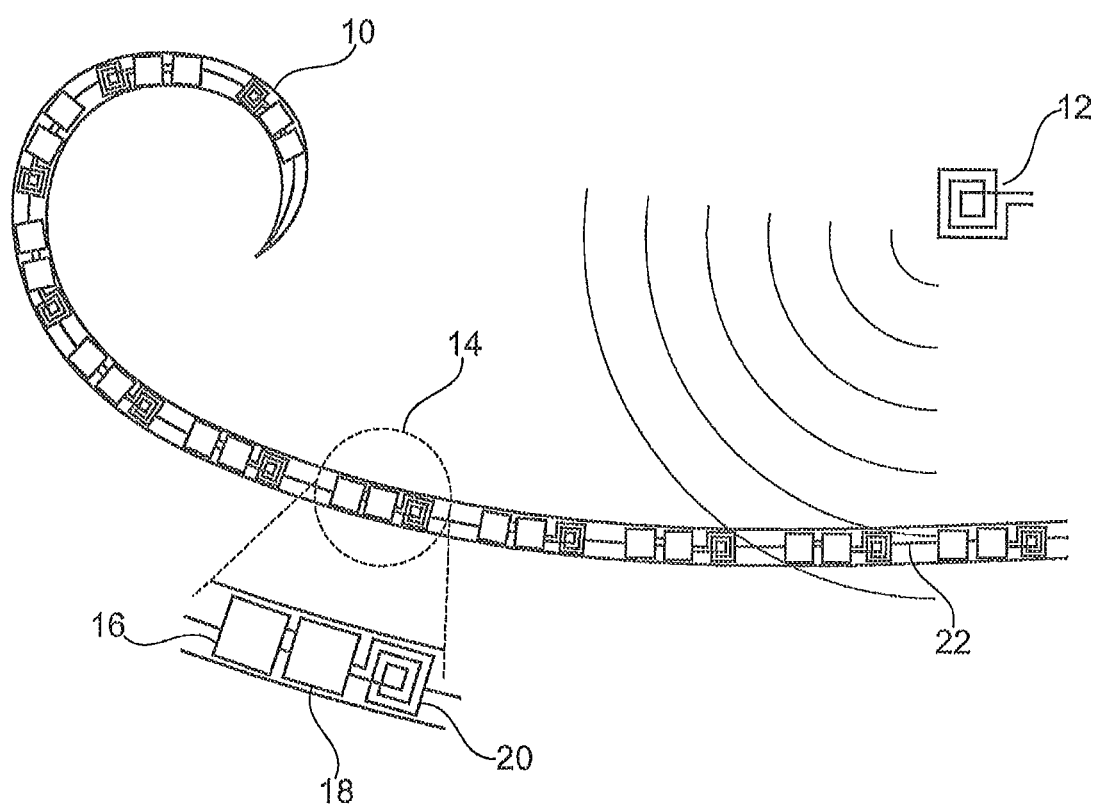

of modules, each of which comprises its own decoder-and-control circuit for decoding module addresses and stimulation signals and generating electric pulses for the electrodes. Encoded module addresses and stimulation signals generated from acoustic signals are applied to inputs of the decoder-and-control circuit.

7 Claims, 2 Drawing Sheets

(51) Int. Cl.
*A61N 1/36* (2006.01)
*H02J 50/05* (2016.01)
*H02J 50/10* (2016.01)

(52) U.S. Cl.
CPC ...... *A61N 1/36171* (2013.01); *A61N 1/36175* (2013.01); *H02J 50/05* (2016.02); *H02J 50/10* (2016.02)

(56) References Cited

U.S. PATENT DOCUMENTS

| | | |
|---|---|---|
| 2002/0029070 A1 | 3/2002 | Leysieffer et al. |
| 2002/0051551 A1* | 5/2002 | Leysieffer .............. A61N 1/375 381/323 |
| 2005/0015133 A1* | 1/2005 | Ibrahim ............... A61N 1/0541 607/137 |
| 2005/0029070 A1 | 2/2005 | Barnes et al. |
| 2013/0148828 A1* | 6/2013 | Fort ....................... H04R 25/30 381/312 |
| 2016/0175590 A1* | 6/2016 | Kulkarni ................ A61N 1/375 607/57 |

OTHER PUBLICATIONS

International Search Report of PCT/DE2016/100342, dated May 16, 2017.

* cited by examiner

COCHLEAR IMPLANT

CROSS REFERENCE TO RELATED APPLICATIONS

This application is the National Stage of PCT/DE2016/100342 filed on Jul. 27, 2016, which claims priority under 35 U.S.C. § 119 of German Application No. 10 2015 114 514.6 filed on Aug. 31, 2015, the disclosure of which is incorporated by reference. The international application under PCT article 21(2) was not published in English.

The invention relates to a cochlear implant.

Cochlear implants that are currently available are limited in terms of their performance capacity by the number of electrodes that can be implemented on them. Each electrode is supplied with energy, on the one hand, and also electronically controlled, on the other hand, by a separate wire, which must be individually guided in the electrode carrier. The electrodes, with power applied to them, stimulate fibers of the auditory nerve. In the cochlea, the distribution of the receptors that are connected with auditory nerve fibers runs in such a manner, for the different sound frequencies, that the high frequencies are detected more toward the base of the cochlear coil, and the low frequencies more toward the apex of the cochlear coil, the helicotrema. This structure is utilized in electrical stimulation (location code).

Typical commercial systems nowadays come to a number of 23 electrodes. A further increase in this number of electrodes is limited by the rigidity of the electrode carrier (cochlear implant). With every additional electrode, the additional wires lead to further stiffening of the electrode carrier, and this makes introduction into the human cochlea more difficult and increases the likelihood of injury to the inner ear. On the other hand, the low number of 23 electrodes is not sufficient to achieve the frequency resolution required for good auditory quality.

A cochlear implant of a cochlear implant system is known from DE 100 18 361 A1. Aside from mentioning an embodiment having electrodes that are mechanically connected with one another and can be inserted into a cochlea in the form of a helix, lined up with one another, for stimulation of receptors of the auditory nerve, the document describes an embodiment with electromechanical transducers as the object for which protection is being claimed. These transducers are also inserted into a cochlea in the form of a helix, lined up with one another, but excite the fluid-filled inner ear spaces of the damaged inner ear by means of a dynamic volume change. In this regard, the transducers are electrically controlled in such a manner that a transducer wave configuration occurs on the basilar membrane of the damaged inner ear, which configuration approximates the type of migration wave formation of a healthy, non-damaged inner ear.

As a further development, the object described in the aforementioned document can contain a decoding logic and converter modules that allow connection of a pole-reduced implant line. Thus, for example, the array connector can consist of only three lines for mass, data, and a cycle signal, wherein the necessary supply with electrical operating energy can take place by means of phantom feed on the cycle signal line.

The invention is based on the task of creating a cochlear implant that comprises more than the number of electrodes usual until now, while maintaining or reducing its rigidity. In addition, the required implanted electronics are supposed to be simplified.

This task is accomplished, in the case of a cochlear implant via the characteristics described herein.

Further developments and advantageous embodiments of the invention are also described herein.

In the invention, the electrodes no longer receive power centrally, by way of separate wires of their own, but rather receive power autonomously, as components of modules having their own decoding and control circuits, in that received coded module addresses and stimulation signals are decoded, evaluated, and carried out. In this way, the possibility is created of reducing the number of wires that supply the modules with electrical energy. In the case of galvanized feed, two wires are sufficient, in the case of inductive or capacitative feed, wires between the individual modules can actually be eliminated. In this way, the rigidity of the cochlear implant is no longer influenced by the number of supplying electrode wires, and is clearly reduced as compared with the previous systems having 23 electrodes.

Module addresses contain information about which module or modules are being addressed and thereby also about which electrodes are receiving power. In this way, the partial frequency band or the partial frequency bands of the auditory spectrum being utilized are selected at the same time.

Stimulation signals contain information about the pulse frequency at which the electrodes are receiving power. The pulse frequency is a measure for the perceived sound level. Furthermore, the stimulation signals can optionally contain information about the pulse amplitude, the pulse/pause ratio, and the pulse shape.

In a first variant, the modules can be galvanically connected with the energy source by way of a common two-wire line.

In this case, the energy source can be disposed detached from the individual modules, and can be optimized for energy storage or for reception of wirelessly received energy.

In a second variant, the modules can be inductively or capacitatively coupled with an energy source that generates an electromagnetic alternating field, wherein each module or each group of at least two modules that are galvanically connected with one another comprises an inductive or capacitative energy reception antenna and a rectifier circuit.

In this variant, each module or modules combined into a group is/are separately supplied with energy. A common galvanic connection of all modules with one is not necessary. The rigidity of the cochlear implant can thereby be reduced even further. Furthermore, the cochlear implant is restricted to the modules lined up with one another and does not require any further components to be implanted, and this clearly reduces the entire implanted component.

Different variants are also possible for data transmission to the individual modules. Thus, the coded module addresses and stimulation signals can be supplied to the inputs of the decoder and control circuit by way of a data bus. This solution makes do with a common receiver for the coded module addresses and stimulation signals to be transmitted to the modules. The module addresses and stimulation signals are passed to all the modules by way of the data bus, and the modules decide on the basis of the module addresses whether or not they are supposed to supply power to the electrodes.

The data bus can consist of the common two-wire line. In this way, it is possible to use the same line not only for energy transmission but also for data transmission.

In another variant, the coded module addresses and stimulation signals can be supplied to the decoder and control circuit, in each instance, by way of a separate receiver having a signal reception antenna, wherein the receiver having the signal reception antenna receives an electromagnetic signal transmitted by a transmitter, which signal is modulated with the coded module addresses and stimulation signals.

Analogous to the advantages of a separate energy supply for every module, a common galvanic connection of all modules with one another is not necessary. The rigidity of the cochlear implant can be reduced even further in this way. Furthermore, the cochlear implant is restricted to the modules that are lined up with one another, and does not require any additional components that must be implanted.

The electromagnetic signal modulated with coded module addresses and stimulation signals can have the same carrier frequency as the energy-transmitting electromagnetic alternating field.

In this case, the transmitter and receiver as well as the transmission and reception antenna only need to be present once, in each instance. In this way, the expenditure for the components to be used is reduced. However, this solution represents a compromise between the penetration depth of the electromagnetic alternating field and the maximally transmissible data rate.

This is not the case if, according to one embodiment, the electromagnetic signal modulated with coded module addresses and stimulation signals has a higher carrier frequency than the energy-transmitting electromagnetic alternating field.

In this case, energy can be transmitted by way of an alternating field at a low carrier frequency, without attenuation that leads to heating due to the body tissue taking place. The coded module addresses and stimulation signals can be transmitted at a high carrier frequency if a high data rate is required for precise selective control of the modules. The higher attenuation as compared with lower frequencies can be accepted, since no supply energy needs to be transmitted, but rather only signals having a power that is sufficient for readability and evaluation. The advantage of high carrier frequencies also consists in that strong bundling is possible by means of an antenna having a high antenna gain, and thereby the high-frequency power can be reduced. Furthermore, the wavelength approaches the maximally possible dimensions of the antennas present in the modules. After all, these dimensions are predetermined by the cochlea.

Figure 2:
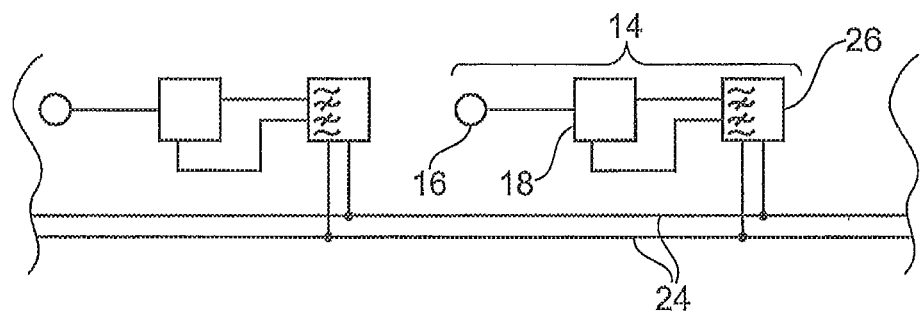
Figure 3:
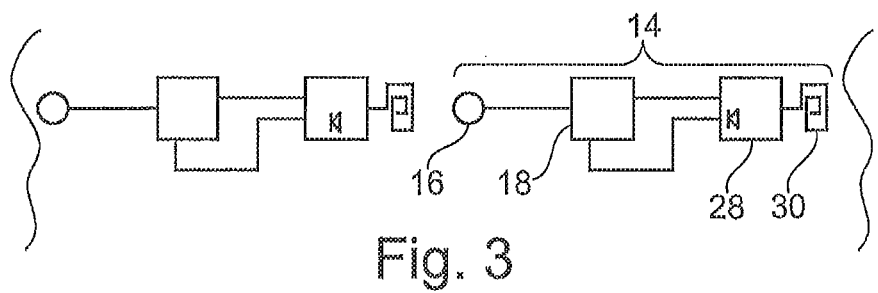
Figure 4:
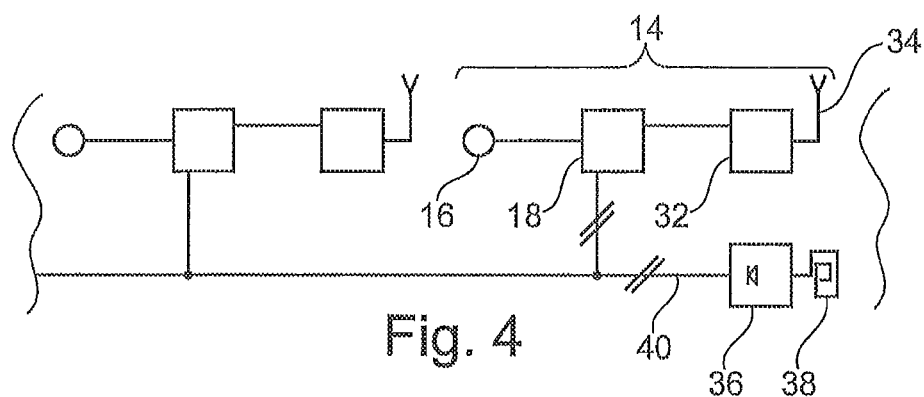

In the following, the invention will be explained using an exemplary embodiment that is shown in the drawing. This shows:

FIG. 1 an exemplary embodiment of the cochlear implant system,

FIG. 2 details of a cochlear implant with data bus,

FIG. 3 details of a cochlear implant with signal and energy transmission on the same frequency for each module separately, and FIG. 4 details of a cochlear implant with signal and energy transmission at different frequencies.

FIG. 1 shows an exemplary embodiment of a cochlear implant system. The cochlear hearing aid system consists of an external part that comprises a microphone, a speech processor, an energy source, and a transmitter having a transmission antenna, as well as of an implanted part. The external part (the speech processor) is generally worn behind the ear, in previously known manner. In FIG. 1, the external part is merely shown in simplified form as a coil symbol 12. The implanted part of the cochlear implant system consists of a helically shaped cochlear implant 10, as well as an energy receiver, not shown here, having a reception antenna and a rectifier.

The cochlear implant 10 comprises modules 14 that in turn each contain an electrode 16, a decoder and control circuit 18, as well as a signal receiver 20 having a reception antenna. The modules 14 are galvanically connected with the energy source, in this case the implanted rectifier, by way of a common two-wire line, and jointly encapsulated.

The electrodes 16 of the modules 14 are disposed adjacent to the fibers of the auditory nerve, and power is applied to them in pulse-like manner, for stimulation of the fibers. Each module 14 represents a partial frequency range of the auditory spectrum being used. The higher the number and spatial density of the modules 14 can be made, the better the resolution of the auditory spectrum being used in partial frequency ranges, or the expansion of the auditory spectrum being used, and this leads to an improvement in auditory quality. The perception of loudness is determined by the amplitude and the total number of current pulses that stimulate the receptors within a certain period of time. Depending on the complexity of the original acoustic signal, one electrode 16 or multiple electrodes can jointly stimulate the auditory nerve fibers. In the case of multiple electrodes, in turn, sequential or quasi parallel provision of power is possible. Quasi parallel is understood to mean a time shift of the control commands that is brought about by serial data transmission and evaluation, and thereby the starts of power application to the electrodes, in terms of time, but this is unimportant physiologically. Even in the physiological condition of an ear having normal hearing, a ti-me offset of excitation along the cochlea comes about ("migration wave").

FIG. 2 shows details of a cochlear implant 10 having a data bus. A continuous data bus 24, which also can be used to supply energy to the individual modules 14, leads to all the inputs of the decoder and control circuits 18. After decoding of the module addresses, it is decided whether or not the respective module is being addressed. If it is being addressed, the stimulation signal is evaluated and converted to current pulses that stimulate the receptors by way of the electrodes 16. The stimulation signal contains information about the pulse frequency, and, optionally, about the pulse/pause ratio, the number of pulses, the pulse amplitude, and the pulse shape. If the wires of the data bus 24 are also being used to supply energy, the coded signals having the module addresses and stimulation signals are separated by way of a switch 26.

FIG. 3 shows details of a, cochlear implant 10 having signal and energy transmission at the same frequency for each module 14 separately. In each module 14, a receiver 28 having a reception antenna 30 is disposed ahead of the decoder and control circuit 18. A signal output of the receiver 28 is connected with an input of the decoder and control circuit 18. An energy output of the receiver 28 is connected with a rectifier, the output of which in turn is connected with an energy supply input of the decoder and control circuit 18.

FIG. 4 shows details of a cochlear implant 10 having signal and energy transmission at different frequencies. In each module 14, a receiver 32 having a reception antenna 34 is disposed ahead of the decoder and control circuit 18. The receiver 32 having the reception antenna 34 is dimensioned for signal transmission at a high carrier frequency. A signal output of the receiver 32 is connected with an input of the decoder and control circuit 18.

An energy receiver 36 having a reception antenna 38 for low frequencies, common to all the modules 14, is present for supplying energy. An energy output of the receiver 36 is connected with a rectifier, the output of which in turn is connected with a two-wire line 40, which forms a loop to all the modules 14.

The invention claimed is:

1. A cochlear implant of a cochlear implant system, comprising:
   electrodes that are mechanically connected with one another and can be inserted into a cochlea strung together in the form of a helix for stimulation of receptors of the auditory nerve;
   a decoder and control circuit that can supply electrical pulses to the individual electrodes, in targeted manner; and
   an energy source;
   wherein the electrodes have electrical signals applied to them by the control circuit in pulses, which signals are generated from the acoustic signals by a processor, and receptors of the auditory nerve that are adjacent to the electrodes are stimulated;
   wherein the electrodes are components of modules, which each comprise their own decoder and control circuit for decoding of module addresses and stimulation signals as well as for generation of electrical pulses for the electrodes; and
   wherein module addresses are encoded to form coded module addresses and the coded module addresses and stimulation signals generated from acoustic signals are applied to inputs of the decoder and control circuit;
   wherein the modules are galvanically connected with each other and with the energy source by way of a common two-wire line.

2. The cochlear implant according to claim 1, wherein the coded module addresses and stimulation signals are passed to the inputs of the decoder and control circuit by way of a data bus.

3. The cochlear implant according to claim 2, wherein the data bus comprises the common two-wire line.

4. A cochlear implant of a cochlear implant system, comprising:
   electrodes that are mechanically connected with one another and can be inserted into a cochlea strung together in the form of a helix for stimulation of receptors of the auditory nerve;
   a decoder and control circuit that can supply electrical pulses to the individual electrodes, in targeted manner; and
   an energy source generating an energy-transmitting electromagnetic alternating field;
   wherein the electrodes have electrical signals applied to them by the control circuit in pulses, which signals are generated from the acoustic signals by a processor, and receptors of the auditory nerve that are adjacent to the electrodes are stimulated;
   wherein the electrodes are components of modules, which each comprise their own decoder and control circuit for decoding of module addresses and stimulation signals as well as for generation of electrical pulses for the electrodes;
   wherein module addresses are encoded to form coded module addresses and the coded module addresses and stimulation signals generated from acoustic signals are applied to inputs of the decoder and control circuit;
   wherein the modules are inductively or capacitatively coupled with the energy source; and
   wherein each module or each group of at least two modules galvanically coupled with one another comprises an inductive or capacitative energy reception antenna and a rectifier circuit.

5. The cochlear implant according to claim 4, wherein the coded module addresses and stimulation signals are supplied to the inputs of the decoder and control circuit by way of a separate receiver having a signal reception antenna, in each instance; an;
   wherein the separate receiver receives an electromagnetic signal transmitted by a transmitter, which signal is modulated with the coded module addresses and stimulation signals.

6. The cochlear implant according to claim 5, wherein the electromagnetic signal modulated with coded module addresses and stimulation signals has the same carrier frequency as the energy-transmitting electromagnetic alternating field.

7. The cochlear implant according to claim 5, wherein the electromagnetic signal modulated with coded module addresses and stimulation signals has a higher carrier frequency than the energy-transmitting electromagnetic alternating field.

* * * * *

UNITED STATES PATENT AND TRADEMARK OFFICE
CERTIFICATE OF CORRECTION

PATENT NO. : 10,668,272 B2  
APPLICATION NO. : 15/744186  
DATED : June 2, 2020  
INVENTOR(S) : Blume et al.

Page 1 of 1

It is certified that error appears in the above-identified patent and that said Letters Patent is hereby corrected as shown below:

In the Claims

In Claim 5, Line 5 (Column 6, Line 30), please change "an;" to --and--.

Signed and Sealed this  
Fourteenth Day of July, 2020

Andrei Iancu  
*Director of the United States Patent and Trademark Office*